United States Patent [19]
Cordier

[11] 4,351,959
[45] Sep. 28, 1982

[54] PROCESS FOR PREPARATION OF ANILINES SUBSTITUTED BY CHLORINE IN THE META-POSITION

[75] Inventor: Georges Cordier, Francheville, France

[73] Assignee: Rhone-Poulenc Agrochimie, Lyons, France

[21] Appl. No.: 116,154

[22] Filed: Jan. 28, 1980

[30] Foreign Application Priority Data

Feb. 15, 1979 [FR] France ................................ 79 04481

[51] Int. Cl.$^3$ ............................................. C07C 85/24
[52] U.S. Cl. ................................... 564/412; 564/315; 564/330; 564/309
[58] Field of Search ............... 260/570 R, 570 D, 580; 564/412, 315, 330, 309

[56] References Cited

U.S. PATENT DOCUMENTS

| | | | |
|---|---|---|---|
| 3,546,297 | 12/1970 | Kosak | 260/580 |
| 3,683,025 | 8/1972 | Pons | 260/580 X |
| 4,085,141 | 4/1978 | Wedemeyer et al. | 260/570 |

*Primary Examiner*—Robert V. Hines
*Attorney, Agent, or Firm*—Browdy & Neimark

[57] ABSTRACT

A process for the dechlorination of aromatic nitro or amino compounds consists in reacting anilines or nitrobenzenes which are polysubstituted by chlorine, with hydrogen, under the action of heat, in the presence of iodide or bromide ions, in the liquid phase and at low pressure.

The process makes it possible selectively to obtain anilines which are chlorine-substituted in the meta-position.

19 Claims, No Drawings

PROCESS FOR PREPARATION OF ANILINES SUBSTITUTED BY CHLORINE IN THE META-POSITION

FIELD OF THE INVENTION

The present invention relates to a process for the preparation of anilines substituted by chlorine in the meta-position, by reacting hydrogen with nitrogen-containing aromatic compounds which are more highly halogen-substituted.

BACKGROUND OF INVENTION

U.S. Pat. No. 4,085,141 describes the preparation of chloroanilines substituted in the meta-position, by reacting polychloroanilines with hydrogen. However, the process described in the said patent requires the use of high pressures and of very large amounts of hydrochloric acid, and this presents serious corrosion problems.

SUMMARY OF THE INVENTION

One object of the invention is to provide a process which makes it possible to prepare anilines substituted in the meta-position by chlorine, with good yields, from nitrogen-containing aromatic compounds which are more highly halogen-substituted.

A further object of the invention is to provide a process for the preparation of anilines substituted in the meta-position by chlorine, it being possible for this process to use either chlorine-substituted nitro compounds (substituted nitrobenzenes and the like) or chlorine-substituted amino compounds (polychloroanilines and the like) as the starting reactant.

A further object of the invention is to provide a process for the preparation of anilines substituted in the meta-position by chlorine, using moderate pressures.

A further object of the invention is to provide a process for the preparation of anilines substituted in the meta-position by chlorine, using moderate reaction temperatures.

Yet another object of the invention is to provide a process for the preparation of anilines substituted in the meta-position by chlorine, using moderately corrosive conditions.

Further objects and advantages of the invention will become apparent in the course of the description which now follows.

DETAILED DESCRIPTION OF EMBODIMENTS

It has now been found that these objects can be achieved by virtue of a process for the preparation of anilines substituted in the meta-position by chlorine, which process consists in carrying out the catalytic hydrogenation of nitrogen-containing benzene derivatives, in the liquid phase, in an acid medium, under the action of heat, under pressure and in the presence of noble metals from group VIII of the periodic classification, and in which process the benzene derivatives have the formula:

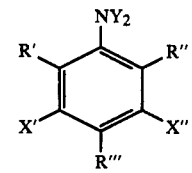

in which: Y represents the hydrogen atom or the oxygen atom, X' and X''', which are identical or different from one another, each represent a chlorine atom or an optionally substituted alkyl, aryl, aralkyl, alkoxy or aralkoxy radical, it being furthermore possible for one of the symbols X' and X''' to be a hydrogen atom (when preparing monochloroanilines (meta-chloroanilines), only one of the substituents X' or X''' represents the chlorine atom, and when preparing dichloroanilines (disubstituted by chlorine in the meta-position), both of the symbols X' and X''' represent the chlorine atom), and R', R'' and R''', which are identical or different from one another, each represent a chlorine atom or an optionally substituted alkyl, aralkyl, alkoxy or aryloxy radical, at least one of these three symbols representing the chlorine atom and it being furthermore possible for at most two of the symbols R', R'' or R''' to be hydrogen, and the reaction is carried out in the presence of iodide and/or bromide ions.

As already stated, the reaction is carried out in the liquid phase; in practice, it is advantageously carried out in the presence of an inorganic or organic solvent which is liquid and inert under the operating conditions. The term inert solvent is understood as meaning a solvent which does not undergo chemical reaction. In fact, the use of water is preferred.

The acidity of the reaction medium is generally such that the pH (in the case of an aqueous medium) is advantageously less than 1.5 and preferably less than 1. The concentration of H+ ions in the medium is generally between 0.5 and 12 g.ions/liter and preferably between 1 and 6 g.ions/liter.

The highest concentrations of acid can be used but no significant advantage is gained.

The acidity of the reaction medium can be achieved by means of strong mineral acids, such as sulphuric, phosphoric or hydrogen halide acids, or strong organic acids; however, it is preferred to use hydrogen halide acids and more especially hydrochloric acid. In any case, in view of the presence of chloride ions originating from the dehalogenation and the presence of iodide or bromide ions which are characteristic of the invention, the reaction is in fact always carried out, at least in part, in the presence of hydrochloric, hydriodic and/or hydrobromic acids. However, insofar as these acids are dissociated in the medium, there is no point in defining the acids used and it is preferable to indicate, as above and below, the acid strength (pH or concentration of H+) and also the nature and the concentration of anions required for the reaction (halide anions).

The process according to the invention is carried out in the liquid phase (with the exception, of course, of the catalyst based on a noble metal, which most commonly constitutes a solid phase). The liquid phase can be homogeneous and constitute a solution; this is a preferred procedure, in particular in the case where Y is an oxygen atom in the formula (I); a liquid phase of this type therefore contains the reactants, the reaction products and the solvent or solvents which may be present. It is also possible to carry out the reaction with two liquid phases.

The pressure at which the reaction is carried out is generally more than 3 bars (relative pressure) and preferably more than 5 bars. There is no critical upper limit for the pressure, but, for economic reasons, it is generally advantageous to operate at pressures of less than 100 bars, pressures of less than 30 bars being preferred.

The reaction temperature is generally between 90° and 300° C. and preferably between 110° and 200° C. In the case where relatively volatile acids are used, an elevated temperature can lead to a relatively high partial pressure of the compounds, other than hydrogen, in the vapour phase (the term vapour phase is obviously understood as meaning the vapour phase above the liquid reaction medium). The operating conditions are generally chosen so that the hydrogen partial pressure is between 10 and 80% of the total pressure (relative pressure) and preferably between 30 and 60%.

The noble metals constituting the base of the catalysts used in the invention are mainly metals from group VIII of the periodic classification, such as ruthenium, rhodium, palladium, osmium, iridium and platinum; palladium is the preferred metal. The metal can be in the metallic form or in the form of a chemical compound; in general, the metal is preferably employed in the metallic form because, under the operating conditions, the compounds tend to be reduced to the metallic form (oxidation state=zero). The catalyst can be supported or unsupported. Any support which is in itself known for supporting catalysts can be used as the catalyst support, provided that this support is resistant to water and acids; activated carbon, silica and barium sulphate may be mentioned as being more particularly suitable as supports; carbon black is a preferred support. Both the catalyst and its support are advantageously in the finely divided form; specific surface areas of more than 100 $m^2/g$ are generally very suitable.

The amount of catalyst employed is such that the proportion by weight of noble metal from the catalyst, relative to the compound of the formula (I) to be treated, is generally between 0.05 and 10% and preferably between 0.5 and 5%.

The iodide and/or bromide ions employed in the reaction can be introduced in the most diverse forms, in particular in the form of hydriodic and/or hydrobromic acids, but it is generally more convenient to introduce them in the form of halides (iodides and/or bromides) or hydrohalides (hydroiodides and/or hydrobromides). The iodides or bromides are usually alkali metal or alkaline earth metal iodides or bromides, such as the iodides or bromides of lithium, sodium, potassium or ammonium. These ammonium salts can be quaternary ammonium salts or non-quaternary ammonium salts (eg. $NH_4^+$). The hydroiodides or hydrobromides are preferably hydroiodides or hydrobromides of a substituted aniline such as the amine of the formula (I) (Y=H) and/or the substituted aniline produced according to the invention. As already stated, chloride ions are formed during the reaction with the result that, from a formal point of view, it is always possible to consider that the reaction takes place in the presence of hydrochloric acid. The amount of iodide ions in the reaction medium is most commonly between $10^{-6}$ and 1 g.ion/liter and preferably between 0.0001 and 0.1 g.ion/liter. The use of small amounts of iodide ions is especially advantageous in that it is generally unnecessary to recover them at the end of the reaction. The amount of bromide ions in the reaction medium is most commonly between 0.01 and 10 g.ions/liter and preferably between 0.1 and 6 g.ions/liter.

The following may preferably be mentioned as compounds of the formula (I) which can be treated by the process of the invention: 2,3-dichloronitrobenzene and 2,3-dichloroaniline, 2,5-dichloronitrobenzene and 2,5-dichloroaniline, 3,4-dichloronitrobenzene and 3,4-dichloroaniline, 2,3,4-trichloronitrobenzene and 2,3,4-trichloroaniline, 2,3,5-trichloronitrobenzene and 2,3,5-trichloroaniline, 2,3,6-trichloronitrobenzene and 2,3,6-trichloroaniline, 2,4,5-trichloronitrobenzene and 2,4,5-trichloroaniline, 3,4,5-trichloronitrobenzene and 3,4,5-trichloroaniline, 2,3,4,6-tetrachloronitrobenzene and 2,3,4,6-tetrachloroaniline, 2,3,4,5-tetrachloronitrobenzene and 2,3,4,5-tetrachloroaniline, 2,3,5,6-tetrachloronitrobenzene and 2,3,5,6-tetrachloroaniline, and pentachloronitrobenzene and pentachloroaniline, but also 4,5,6-trichloro-2-methylnitrobenzene and 4,5,6-trichloro-2-methylaniline, 2,5-dichloro-4-methylnitrobenzene and 2,5-dichloro-4-methylaniline, 2,3,5,6-tetrachloro-4-methylnitrobenzene and 2,3,5,6-tetrachloro-4-methylaniline, 2,5-dichloro-3,4-dimethylnitrobenzene and 2,5-dichloro-3,4-dimethylaniline, 2,5-dichloro-4-ethylnitrobenzene and 2,5-dichloro-4-ethylaniline, 2,5-dichloro-4-propylnitrobenzene and 2,5-dichloro-4-propylaniline, 3,4,6-trichloro-2-benzylnitrobenzene and 3,4,6-trichloro-2-benzylaniline, 2,2'-dinitro-3,5,6,3',5',6'-hexachlorodiphenylmethane and 2,2'-diamino-3,5,6,3',5',6'-hexachlorodiphenylmethane, 2-nitro-3,4,5-trichlorodiphenyl and 2-amino-3,4,5-trichlorodiphenyl, 4,4'-dinitrooctachlorodiphenyl and 4,4'-diaminooctachlorodiphenyl, 4,5-dichloro-2-methoxynitrobenzene and 4,5-dichloro-2-methoxyaniline, 3,4-dichloro-2-methoxynitrobenzene and 3,4-dichloro-2-methoxyaniline, 3,6-dichloro-2-methoxynitrobenzene and 3,6-dichloro-2-methoxyaniline, 5,6-dichloro-2-methoxynitrobenzene and 5,6-dichloro-2-methoxyaniline, 3,4,6-trichloro-2-methoxynitrobenzene and 3,4,6-trichloro-2-methoxyaniline, 3,4,5-trichloro-2-methoxynitrobenzene and 3,4,5-trichloro-2-methoxyaniline, 3,4,5,6-tetrachloro-2-methoxynitrobenzene and 3,4,5,6-tetrachloro-2-methoxyaniline, 4,5-dichloro-3-methoxynitrobenzene and 4,5-dichloro-3-methoxyaniline, 5,6-dichloro-3-methoxynitrobenzene and 5,6-dichloro-3-methoxyaniline, 2,5-dichloro-3-methoxynitrobenzene and 2,5-dichloro-3-methoxyaniline, 4,5,6-trichloro-3-methoxynitrobenzene and 4,5,6-trichloro-3-methoxyaniline, 2,4,5,6-tetrachloro-3-methoxynitrobenzene and 2,4,5,6-tetrachloro-3-methoxyaniline, 2,3-dichloro-4-methoxynitrobenzene and 2,3-dichloro-4-methoxyaniline, 2,5-dichloro-4-methoxynitrobenzene and 2,5-dichloro-4-methoxyaniline, 2,3,6-trichloro-4-methoxynitrobenzene and 2,3,6-trichloro-4-methoxyaniline, 2,3,5-trichloro-4-methoxynitrobenzene and 2,3,5-trichloro-4-methoxyaniline, 2,3,5,6-tetrachloro-4-methoxynitrobenzene and 2,3,5,6-tetrachloro-4-methoxyaniline, 4,5-dichloro-2-phenoxynitrobenzene and 4,5-dichloro-2-phenoxyaniline, 3,4,5,6-tetrachloro-2-phenoxynitrobenzene and 3,4,5,6-tetrachloro-2-phenoxyaniline, 2,4,5,6-tetrachloro-3-phenoxynitrobenzene and 2,4,5,6-tetrachloro-3-phenoxyaniline, 2,5-dichloro-4-phenoxynitrobenzene and 2,5-dichloro-4-phenoxyaniline, and 2,3,5,6-tetrachloro-4-phenoxynitrobenzene and 2,3,5,6-tetrachloro-4-phenoxyaniline.

The following may preferably be mentioned amongst the anilines which are substituted in the meta-position by a chlorine atom and can be prepared by the process according to the invention: meta-chloroaniline and 3,5-dichloroaniline, but also: 5-chloro-2-methylaniline, 5-chloro-3-methylaniline, 3-chloro-4-methylaniline, 3,5-dichloro-4-methylaniline, 5-chloro-3,4-dimethylaniline, 3-chloro-4-ethylaniline, 3-chloro-2-benzylaniline, 4,4'-diamino-2,6,2',6'-tetrachlorodiphenyl, 3-chloro-2-methoxyaniline, 5-chloro-2-methoxyaniline, 3,5-dichloro-2-methoxyaniline, 3-chloro-4-methoxyaniline, 5-chloro-3-methoxyaniline, 3,5-dichloro-4-methoxyaniline, 3-chloro-2-phenoxyaniline, 5-chloro-2-phenoxyaniline, 3,5-dichloro-2-phenoxyaniline and 3,5-dichloro-4-phenoxyaniline.

The process according to the invention can be carried out continuously or discontinuously. At the end of the reaction, the catalyst can be separated off, if necessary, by filtration or by equivalent means such as draining; the amine prepared, which is chlorine-substituted in the meta-position, can be separated off by any means which is in itself known, e.g. by solvent extraction and/or by distillation; before carrying out this separation, it is generally appropriate to convert the amine (salified in an acid medium) back into the form of an (unsalified) amine by rendering the reaction mixture neutral or alkaline with the aid of an alkaline agent. In the case of a process which uses bromine ions, it can be advantageous to recover these ions in order to recycle them into a subsequent operation.

The process according to the invention is very advantageous because of its good selectivity with respect to the amine which is chlorine-substituted in the meta-position, and because of the relatively mild conditions under which it can be carried out. The amines produced in this way, which are chlorine-substituted in the meta-position, can be used, in particular, for manufacturing pesticides.

The following examples, which are given without implying a limitation, illustrate the invention and show how it can be put into effect.

EXAMPLE 1

2,3,4,5-Tetrachloroaniline (1.67 g), a catalyst consisting of palladium deposited on activated carbon (specific surface area of the activated carbon: 1,100 m$^2$/g; proportion of palladium by weight: 10%) (0.07 g), an aqueous solution of hydrochloric acid having a concentration of 4 mols/liter (106 cc) and an aqueous solution of hydriodic acid having a concentration of 7.6 mols/liter (13.3 cc) are introduced into a 250 cc autoclave coated on the inside with tantalum.

The autoclave is closed and purged first with argon and then with hydrogen. The temperature is then raised to 190° C., whilst allowing the autogenous pressure to increase, and then, when this temperature has been reached, hydrogen is introduced until the total (relative) pressure is 20 bars, the hydrogen partial pressure being 6 bars.

The reaction is allowed to proceed under these conditions for 1 hour. After cooling, the liquid reaction mixture is rendered alkaline with an aqueous solution of sodium hydroxide (NaOH); the catalyst is filtered off; the 3,5-dichloroaniline is extracted from the aqueous phase using methylene chloride; the methylene chloride solution thus obtained is dried over sodium sulphate; the solvent is evaporated off in vacuo; the degree of conversion of the tetrachloroaniline was 100% and the yield of 3,5-dichloroaniline was 98.2%.

EXAMPLE 2

Example 1 is repeated with the following modifications: an aqueous solution of hydrochloric acid having a concentration of 0.8 mol/liter (98 cc) (instead of a solution having a concentration of 4 mols/liter (106 cc)) is used and dry NaI (63 g) (instead of a solution of HI (13.3 cc)) is used.

3,5-Dichloroaniline is obtained with a yield of 92.2%. The degree of conversion of the tetrachloroaniline is 100%.

EXAMPLE 3

Example 1 is repeated with the following modifications: an aqueous solution of hydrochloric acid having a concentration of 0.8 mol/liter (115 cc) (instead of a solution having a concentration of 4 mols/liter (106 cc)) is used and dry NaI (14.8 g) (instead of a solution of HI (13.3 cc)) is used.

3,5-Dichloroaniline containing 5.8% of trichloroaniline and 0.3% of meta-chloroaniline is obtained; the yield of dichloroaniline is 93.6%; the degree of conversion of the tetrachloroaniline is 100%.

EXAMPLE 4

Example 1 is repeated with the following modifications: an aqueous solution of hydrochloric acid (120 cc instead of 106 cc) is used, an aqueous solution of hydriodic acid having a concentration of 0.01 mol/liter (0.4 cc) (instead of a solution having a concentration of 7.6 mols/liter (13.3 cc)) is used and the reaction lasts 5 hours (instead of 1 hour).

3,5-Dichloroaniline containing 3.5% of meta-chloroaniline is obtained with a yield of 96% of 3,5-dichloroaniline and a degree of conversion of the tetrachloroaniline of 100%.

EXAMPLE 5

Example 1 is repeated with the following modifications: tetrachloroaniline (0.42 g instead of 1.67 g) is introduced, an aqueous solution of hydrochloric acid having a concentration of 2.5 mols/liter (120 cc) (instead of a solution having a concentration of 4 mols/liter (106 cc)) is introduced, dry KI (0.11 g) (instead of a solution of HI (13.3 cc)) is introduced, the reaction lasts 2 hours 40 minutes (instead of 1 hour), the temperature is 150° C. (instead of 190° C.) and the pressure is 10 bars, the hydrogen partial pressure being 5 bars.

3,5-Dichloroaniline containing 2.5% of aniline and 2.5% of meta-chloroaniline is obtained with a yield of 3,5-dichloroaniline of 86%. Degree of conversion of the tetrachloroaniline: 100%.

EXAMPLE 6

Example 1 is repeated with the following modifications: 2,3-dichloroaniline (1.17 g) (instead of tetrachloroaniline) is used, a palladium-based catalyst (0.56 g instead of 0.07 g) is used, an aqueous solution of HCl having a concentration of 2.5 mols/liter (120 cc) (instead of a solution of HCl having a concentration of 4 mols/liter (106 cc)) is used and KI (0.2 g) (instead of hydriodic acid) is added.

The temperature is raised to 160° C.; the total pressure is 13 bars (the hydrogen partial pressure being 6 bars); the reaction time is 3 hours.

The degree of conversion of the 2,3-dichloroaniline is 98.2%; the yield of meta-chloroaniline is 95.6%, relative to the dichloroaniline converted.

EXAMPLE 7

Example 6 is repeated with the following modifications: 3,4-dichloroaniline (instead of 2,3-dichloroaniline) is used, hydrochloric acid having a concentration of 1 mol/liter (instead of 2.5 mols/liter) is used, KI (0.04 g instead of 0.2 g) is used and the reaction time is only 45 minutes.

The 3,4-dichloroaniline is completely converted; meta-chloroaniline is obtained with a yield of 97.1%.

EXAMPLE 8

3,4-Dichloronitrobenzene (139 g), a catalyst (palladium on carbon black, containing 10% of palladium) (0.56 g), an aqueous solution of hydrochloric acid having a concentration of 1 mol/liter (120 cc) and KI (0.04 g) are introduced into a 225 cc autoclave.

The autoclave is purged with argon and then with hydrogen, and hydrogen is introduced into the autoclave until the pressure is 4 bars. The temperature of the autoclave is raised to 160° C. The pressure is then 13 bars, the hydrogen partial pressure being 6 bars.

The reaction is allowed to proceed for 1 hour 40 minutes and the autoclave is cooled. The degree of conversion of the dichloronitrobenzene is 100%. Meta-chloroaniline was obtained with a yield of 92.9%.

EXAMPLE 9

A 4 N aqueous solution of hydrochloric acid (120 cc), 3,4,5-trichloroaniline (0.354 g), a palladium-based catalyst such as that used in Example 1 (0.14 g) and KI (0.011 g) are introduced into a 250 cc autoclave coated on the inside with tantalum.

The autoclave is closed and purged with argon and then with hydrogen. It is heated at 130° C. for 2 hours 30 minutes under a total pressure of 8 bars and a hydrogen partial pressure of 5 bars. During the reaction, the trichloroaniline was entirely converted and 3,5-dichloroaniline was obtained with a yield of 99%.

EXAMPLE 10

A 4 N aqueous solution of HCl (120 cc), 2,4,5-trichloroaniline (3.54 g), a palladium-based catalyst such as that used in the preceding examples (palladium on activated carbon containing 10% of palladium) (1.4 g) and potassium iodide (0.011 g) are introduced into a 250 cc autoclave coated on the inside with tantalum.

The autoclave is closed and purged with argon and then with hydrogen. It is heated at 160° C. for 240 minutes under a total pressure of 18 bars and a hydrogen partial pressure of 13 bars.

The conversion is complete and 3-chloroaniline is obtained with a yield of 98.2%.

EXAMPLE 11

The procedure of the preceding example is followed, except for the following conditions:

A 4 N aqueous solution of HCl (120 cc), 2,3,5-trichloroaniline (0.354 g), a palladium-based catalyst (palladium on carbon activated containing 10% of palladium) (0.140 g) and potassium iodide (0.011 g) are introduced.

The autoclave is heated at 160° C. for 160 minutes under a total pressure of 18 bars, the hydrogen pressure being 13 bars.

The conversion is complete and 3,5-dichloraniline is obtained with a yield of 96.8%.

EXAMPLE 12

The procedure of Example 1 of the patent is followed, except for the following conditions:

An aqueous solution of hydrochloric acid containing 4 mols/liter (120 cc), 2,3,4,5-tetrachloroaniline (1.67 g), the catalyst used in Example 1 (0.07 g) and potassium bromide (7.14 g) are introduced.

The autoclave is heated at 190° C. for 170 minutes under a total pressure of 20 bars, the hydrogen pressure being 6 bars.

The conversion is total. 3,5-Dichloroaniline is obtained with a yield of 90%.

EXAMPLE 13

The procedure of Example 1 is followed, except for the following conditions:

4 N aqueous hydrochloric acid (120 ml), 2,3,4,5-tetrachloroaniline (420 mg), the catalyst used in Example 1 (140 mg) and potassium iodide (1.1 mg, i.e. a concentration of $5.5 \cdot 10^{-5}$ in the medium) are introduced.

The autoclave is heated at 160° C. for 220 minutes under a total pressure of 9 bars, the hydrogen pressure being 4.5 bars.

The conversion of the tetrachloroaniline is complete. 3,5-Dichloroaniline is obtained with a yield of 92.5%.

EXAMPLE 14

The procedure of Example 1 is followed, except for the following conditions:

4 N aqueous hydrochloric acid (120 ml), 2,3,4,5-tetrachloroaniline (420 mg), a catalyst containing 1.1% of palladium deposited on activated carbon (140 mg) and potassium iodide (11 g) are introduced.

The autoclave is heated at 160° C. for 180 minutes under a total pressure of 18 bars, the hydrogen pressure being 13 bars. 3,5-Dichloroaniline is obtained with a yield of 98.1%. The conversion of the tetrachloroaniline is complete.

EXAMPLE 15

The same result as in Example 14 is obtained, using the same starting materials and the same conditions, by replacing the catalyst containing 1.1% of palladium (140 mg) by a catalyst containing 2.8% of palladium deposited on the same support by the same method (140 mg).

EXAMPLE 16

A 13.6% strength aqueous solution of hydrochloric acid (2 kg), a catalyst consisting of palladium deposited on activated carbon (specific surface area of the carbon black: 1,100 m$^2$/g; proportion of palladium by weight: 10%) (150 g) and dry solid potassium iodide (11.7 g, i.e. 0.5 g.ion of iodide ion per gram atom of palladium) are introduced into a 3.6 liter autoclave coated on the inside with tantalum.

The autoclave is closed and purged first with nitrogen and then with hydrogen. Hydrogen is then injected until the pressure is 3 bars. The temperature is raised to 160° C., whilst allowing the autogenous pressure to increase. Further hydrogen is injected in order to establish a pressure of 15.5 bars, the hydrogen partial pressure being 10 bars. 2,3,4,5-Tetrachloronitrobenzene (1 mol) is then injected in the course of 2 hours 30 minutes.

The reaction is allowed to proceed under these conditions for 2 hours, whilst stirring. The reactor is cooled to 100° C. and then emptied; the liquid reaction medium is neutralised with aqueous sodium hydroxide; the catalyst is filtered off and the chlorine-substituted amines, mainly 3,5-dichloroaniline, are extracted with toluene. The solvent is evaporated off in vacuo.

Under these conditions, the degree of conversion of the 2,3,4,5-tetrachlorobenzene is 100% and the yield of 3,5-dichloroaniline is 94%.

I claim:

1. A process for the preparation of anilines substituted in the meta-position by chlorine, by the catalytic hydrogenation of chlorine-substituted nitrogen-containing benzene derivatives, in the liquid phase, in an acid medium, under the action of heat, under pressure and in the presence of noble metals from group VIII of the periodic classification, in which process the benzene derivatives have the formula:

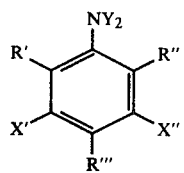

in which Y represents the hydrogen atom or the oxygen atom, X' and X'', which are identical or different from one another, each represent a chlorine atom or an optionally substituted alkyl, aryl, aralkyl, alkoxy or aralkoxy radical or one of X' and X'' in hydrogen, and R', R'' and R''', which are identical or different from one another, each represent a chlorine atom or an optionally substituted alkyl, aralkyl, alkoxy or aryloxy radical, at least one of these three representing the chlorine atom and at most two of R', R'' and R''' being hydrogen, and the reaction is carried out in an aqueous medium in which the pH is less than 1.5 and/or the concentration of $H^+$ ions in the aqueous reaction medium is between 0.5 and 12 g.ions/liter, in the presence of iodide and/or bromide ions and in which the proportion of iodide ions in the reaction medium is at least $10^{-6}$ g.ions/liter and/or the proportion of bromide ions in the reaction medium is at least 0.01 g.ion/liter.

2. A process according to claim 1, in which R', R'', R''', X' and X'', which are identical or different from one another, represent the hydrogen atom or the chlorine atom.

3. A process for the preparation of optionally substituted meta-dichloranilines, according to one of claims 1 or 2, in which X' and X'' represent the chlorine atom.

4. A process for the preparation of optionally substituted meta-monochloroanilines, according to one of claims 1 or 2, in which only one of the two radicals X' and X'' is the chlorine atom.

5. A process for the preparation of 3,5-dichloroaniline, according to claim 1, in which Y is the hydrogen or oxygen atom, X' and X'' are the chlorine atom and R', R'' and R''' are the hydrogen atom or the chlorine atom, at least one of them being the chlorine atom.

6. A process according to claim 1, in which the pH is less than 1 and/or the concentration of $H^+$ ions in the reaction medium is between 1 and 6 g/ions/liter.

7. A process according to claim 1, in which the reaction medium consists only of a liquid phase, except for the catalyst based on a noble metal.

8. A process according to claim 1, in which the total pressure is between 3 and 100 bars.

9. A process according to claim 10, in which the total pressure is between 5 and 30 bars.

10. A process according to claim 1, in which the temperature is between 90° and 300° C.

11. A process according to claim 1, in which the hydrogen partial pressure is between 10 and 80% of the total pressure.

12. A process according to claim 10, in which the hydrogen partial pressure is between 30 and 60% of the total pressure.

13. A process according to claim 1, in which the noble metal catalyst is palladium.

14. A process according to claim 1, in which the proportion by weight of noble metal, relative to the compound of the formula (I), is between 0.05 and 10%.

15. A process according to claim 1, in which the proportion of iodide ions in the reaction medium is between $10^{-6}$ and 1 g.ion/liter and/or the proportion of bromide ions in the reaction medium is between 0.01 and 10 g.ions/liter.

16. A process according to claim 14, in which the proportion of iodide ions in the reaction medium is between 0.0001 and 0.1 g.ion/liter and/or the proportion of bromide ions is between 0.1 and 5 g.ion/liter.

17. A process according to claim 1, in which the temperature is between 110° and 200° C.

18. A process according to claim 7, in which the proportion by weight of noble metal catalyst, relative to the compound of formula (I), is between 0.5 and 5%.

19. A process according to claim 2 or 5, in which the reaction medium consists only of a liquid phase, except for the catalyst bseed on a noble metal; the total pressure is between 3 and 30 bars; the temperature is between 90° and 200° C.; the hydrogen partial pressure is between 10 and 80% of the total pressure; and the noble metal catalyst is palladium present in an amount between 0.05 and 10% relative to the compound of formula (I).

* * * * *

UNITED STATES PATENT AND TRADEMARK OFFICE
CERTIFICATE OF CORRECTION

PATENT NO. : 4,351,959
DATED : Sept. 28, 1982
INVENTOR(S) : Cordier, Georges

It is certified that error appears in the above-identified patent and that said Letters Patent are hereby corrected as shown below:

IN THE CLAIMS

Column 10, line 23, change "10" to read --11--; column 10, line 36, change "14" to read --15--.

Signed and Sealed this

Twenty-fourth Day of May 1983

[SEAL]

Attest:

DONALD J. QUIGG

Attesting Officer

Acting Commissioner of Patents and Trademarks